United States Patent [19]

Hakala et al.

[11] 4,382,806
[45] May 10, 1983

[54] METHOD FOR SEPARATING WATER FROM A GAS SAMPLE

[75] Inventors: Matti A. Hakala; Antti L. J. Martikainen, both of Helsinki; Jorma J. Auvinen, Nummela, all of Finland

[73] Assignee: Instrumentarium Oy, Helsinki, Finland

[21] Appl. No.: 285,261

[22] Filed: Jul. 20, 1981

Related U.S. Application Data

[62] Division of Ser. No. 71,562, Aug. 31, 1979, Pat. No. 4,304,578.

[30] Foreign Application Priority Data

Sep. 1, 1978 [FI] Finland .................................. 782693
Jun. 1, 1979 [FI] Finland .................................. 791769

[51] Int. Cl.³ ............................................. B01D 51/06
[52] U.S. Cl. ........................................... 55/18; 55/55
[58] Field of Search ................... 55/189, 190, 192, 18, 55/55, 57, 270; 73/19, 23, 29, 421.5 R; 128/718, 719; 210/513, 532.1; 422/84

[56] References Cited

U.S. PATENT DOCUMENTS

4,147,500 4/1979 Karlsoen .............................. 55/270
4,197,858 4/1980 Osborn ................................ 128/719

Primary Examiner—Ivars C. Cintins
Attorney, Agent, or Firm—Andrus, Sceales, Starke & Sawall

[57] ABSTRACT

A method of separating water from a gas sample. The gas sample is conducted from a patient to a water separating chamber having a tapered lower end. A continuous branch flow is produced from the gas sample for the separation of water, and the branch flow with the separated water is discharged from the lower end of the chamber to a first outlet by applying a vacuum to the first outlet. The gas is continuously withdrawn from the upper end of the chamber through a second outlet by applying a vacuum to said second outlet. The flow through the respective outlets is regulated so that the flow through the first outlet is preferably less than the flow through the second outlet.

2 Claims, 2 Drawing Figures

METHOD FOR SEPARATING WATER FROM A GAS SAMPLE

This is a division of application Ser. No. 06/071,562, filed Aug. 31, 1979, now U.S. Pat. No. 4,304,578.

BACKGROUND OF THE INVENTION

When for instance a $CO_2$ analyzer is used in measurement of respiration air, a problem is imposed by the water vapour present in the exhaled air. Since the temperature in the sample duct is lower than human body temperature, the water vapour will condense in the measuring instrument and the measurement may fail due to introduction of water droplets in the measuring chamber.

To the end of removing water from the sampled gas there has in gas analyzers of prior art been used a water separator wherein the condensing water is collected in a small cup, which is emptied as needed. This design solution of prior art is encumbered by the following drawbacks. The ascent time in the measurement increases, which is not desirable since the analyzer should be able to follow the changes of $CO_2$ content during the different phases of respiration. For this reason endeavours should be to minimize the volume of the cup, but this causes the need for frequent emptying. If one forgets to empty the cup in time, the result will be failure of the measurement.

SUMMARY OF THE INVENTION

The object of the invention is to provide an automatically emptying water separator by which it is possible to solve the problems mentioned.

This aim is achieved according to the invention in that in the water separation chamber the sample flow has been arranged to branch into two partial flows such that the main flow is drawn through the measuring chamber by means of a tube connecting with the upper part of the water separation chamber and a small side flow is continuously drawn through a tube connecting with the lower part of the water separation chamber.

It is then possible to reduce the volume of the water separation chamber considerably, whereby the speed of ascent of the measurement correspondingly improves. At the same time that advantage is gained that the regular emptying of the water separator is obviated, or it is possible to use a separate, large water collecting vessel with long emptying intervals.

A particularly advantageous embodiment of the invention is characterized in that the water suspension chamber is divided into lower and upper chamber parts communicating with each other, to the lower part of the water separation chamber having been connected the sample entry tube and the side flow tube, and the main flow tube connecting with the upper chamber part, and that the side flow tube opens, together with the suction tube connecting with the pump, into a detachable or otherwise emptiable condensate collecting vessel, through which the subatmospheric pressure producing the side flow acts on the tube connecting with the lower part of the water separation chamber.

The aim in this further developing work was to reduce even more the dead volume in the sample passage, which would enable the sample quantity to be made smaller without incurring any prohibitively long ascent time in the measurement, while retaining sufficient water separation capacity at the same time. There will then be no necessity for the condensate to pass through the pump, and one may use as pumps for producing the main as well as the side flow, inexpensive commercially available diaphragm pumps, which can be obtained complete with two pumps built into one housing. It is possible by means of throttling units inserted before or after the pumps, to control the proportions of main and side flow. In order that the sample quantity might not be substantially influenced by the side flow, the side flow is considerably less-most appropriately about 5% of the total sample flow.

In this result of the further development of the invention the chamber parts themselves can be manufactured with extreme ease in that they are formed at the boundary surface between two bodies fixed together with gas-tight joint, and whereat depressions, with conical shape for instance, have been provided in both bodies. To one of these two bodies the detachable condensate collecting vessel may be attached, by threads for instance.

DESCRIPTION OF THE DRAWINGS

In the following the invention is illustrated with reference made to the attached drawings, wherein.

DESCRIPTION OF THE ILLUSTRATED EMBODIMENT

Figure 1:
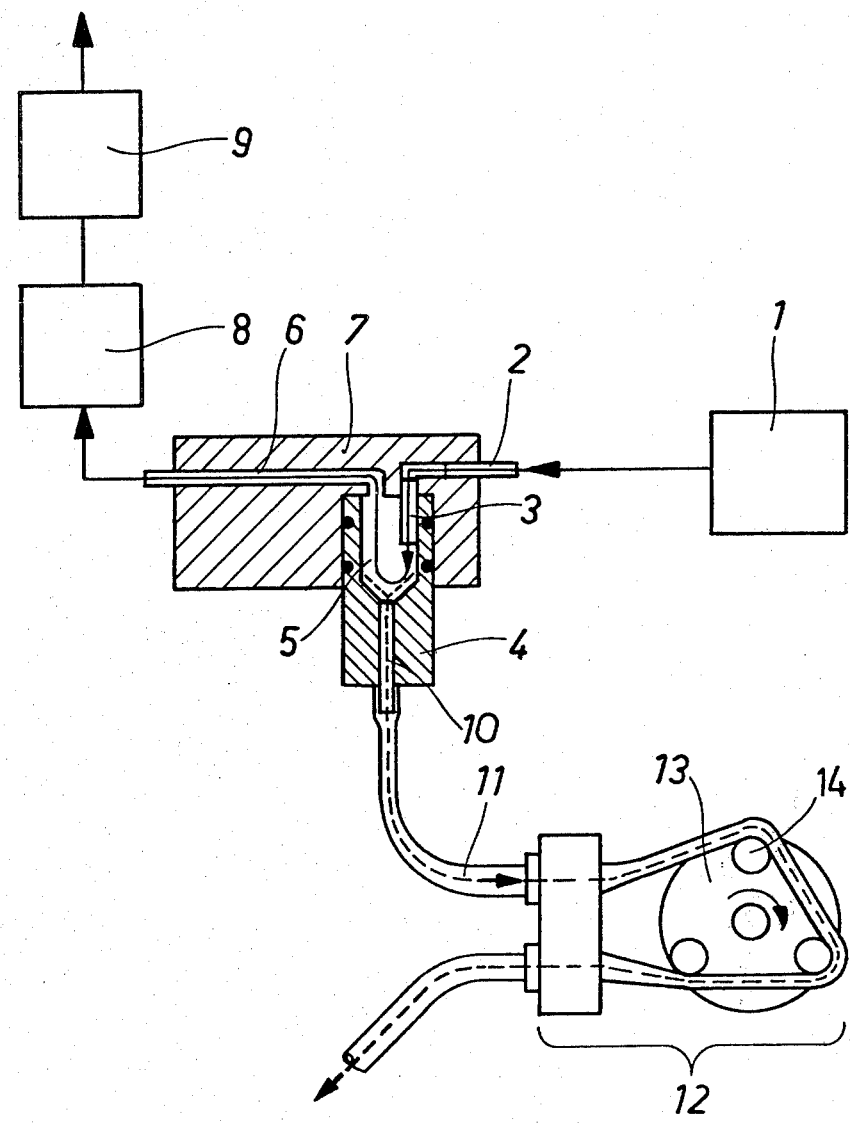
FIG. 1 presents a water separator according to the invention, connected to a gas analyzer which has not been depicted, merely the measuring chamber 8 thereof being shown.

In FIG. 1, the gas flow has been indicated by a solid line and the water flow, by an interrupted line. The apparatus is being described as a $CO_2$ analyzer for use in analysing respiration air. From the patient 1, the gas sample is conducted into the analyzer through the duct 2, which ends in a downwardly pointing tube 3 opening into the interior 5 of the cuvette 4. The cuvette 4 has been pushed with tight seal into a hollow space provided in the frame body 7, from the upper part of which the exit duct continues through the frame body 7. The direction of the tube 3 has been chosen to make sure that the gas will be blown downwardly and has to travel along a U-shaped path in the interior 5 of the chamber before leaving the water separator. Hereby the condensed water present in the gas will precipitate on the inner surfaces of the chamber 5. The gas sample from which the condensed water has been separated is conducted from the duct 6 to the measuring chamber 8, where the $CO_2$ content of the gas is measured in a manner known in itself in the art. From the measuring chamber 8, the gas is voided into room space by the aid of an air pump 9.

As taught by the invention, dewatering is continuous from the cuvette 4. The hollow space 5 tapers at its lower end to the water draining tube 10, which has been connected to the flexible draining tube 11. This latter, again, connects to a flexible tube pump 12 known in itself, where a bight or loop formed of the flexible tube 11 is acted on by pumping members 14 rotatably carried on a rotating member 13 and which flatten the tube and as they rotate move the squeezing or flattening point in the sucking direction to the purpose of producing in the tube 11 a vacuum giving rise to suction. It is possible by regulating the speed of rotation of the member 13, to control the suction capacity.

Figure 2:
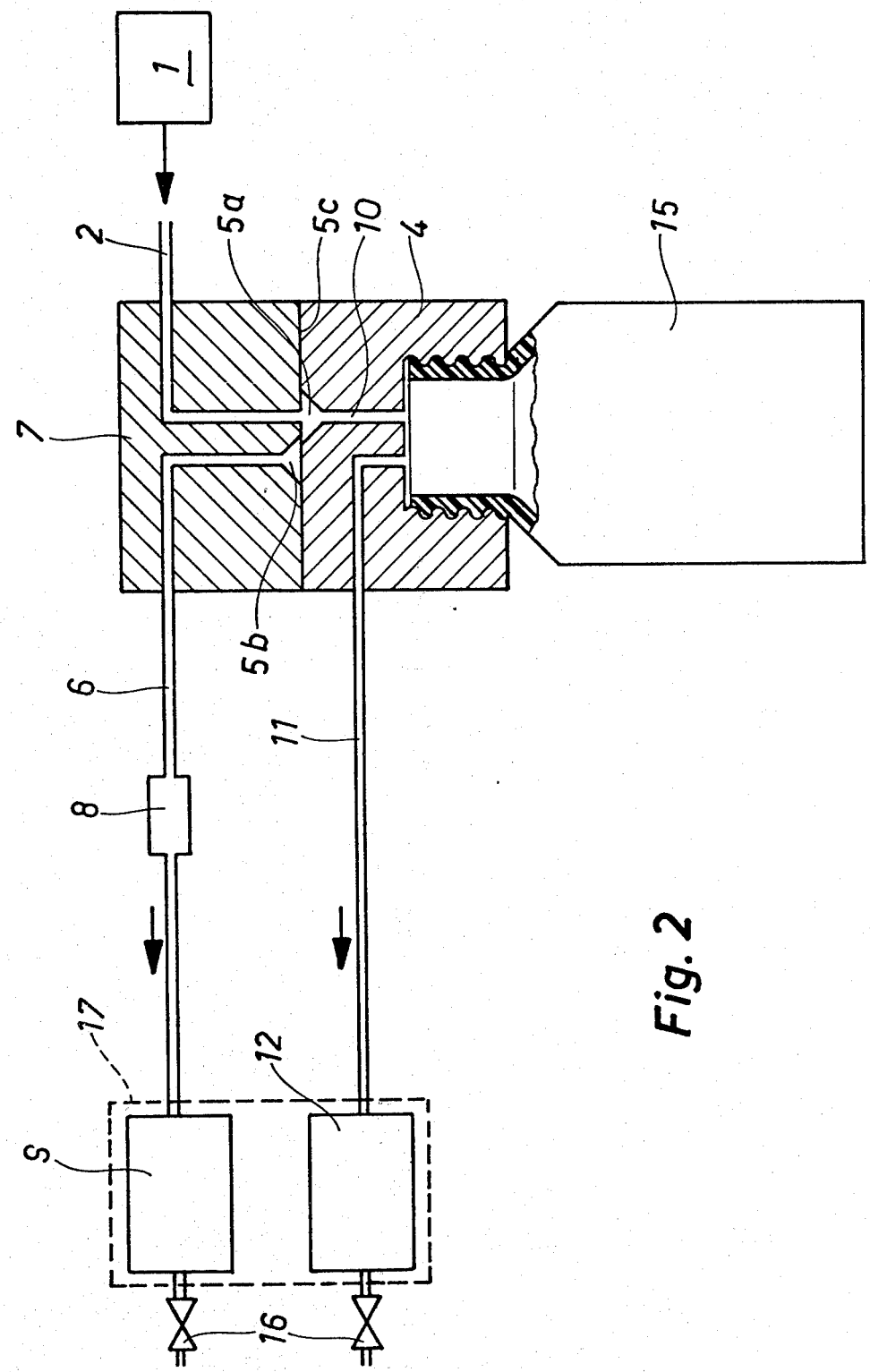
FIG. 2 illustrates a modified form of the invention.

In the embodiment of FIG. 2, the part of the flexible tube pump subject to wear has been eliminated: its flexible tube, and the water separator has been carried out with simpler and less expensive components. The gas sample is carried from the patient 1 through the tube 2 into the part 5a of the water separation chamber, where it is divided into two partial flows. The main flow is drawn by the pump 9 through the chamber part 5b, the tube 6 and the measuring chamber 8. About 5% of the sample flow are drawn by the pump 12 through the tube 10, water collecting vessel 15 and tube 11. The water separation chamber has been formed on the boundary surface 5c between two bodies 4 and 7 joined together with gas-tight seal, this having been done by making in both bodies 4,7 a conical depression 5a and 5b, respectively.

The bodies 4,7 are placed in register so that the cones 5a and 5b will be eccentric with reference to each other. The saside flow carrying the water off starts from the apex of the lower cone 5a, where the tube 10 connects. The sample entry port, that is the point where the tube 2 opens, is located at the same point in the upper half 7. The outflow of the main sample flow, again, is from the top of the upper cone 5b, where the tube 6 connects.

One achieves by the design now described that the water droplets arriving in the chamber part are inherently directed into the downward flow, into tube 10. The volume of the chamber parts 5a,5b may then be made very small and therefore no mixing of the sample occurs in them, which would increase the ascent time in the measurement.

The pumps 9 and 12 are common diaphragm pumps. In the present case a commercially available design has been employed, in which both pumps have been accommodated in one housing 17 and consist of two diaphragms, the movement of which is controlled by one electromagnet. The flows are adjusted to be appropriate, by means of throttling elements 16 provided on the delivery side of the pumps.

The water collecting vessel 15 may be a transparent plastic or glass flask attached by threads to the lower chamber body 4 and which can be detached for emptying. The size of the collecting vessel 15 may be selected as desired, without any detrimental effect on the measurement, and hereby the chance is afforded to increase substantially the collecting vessel emptying intervals.

We claim:

1. A method of respiratory gas analysis, comprising the steps of conducting a gas sample from a patient into a water separating chamber having a tapered lower end, separating the water from the gas in said chamber, continuously withdrawing the separated water from the lower end of the chamber through a water outlet conduit by applying sub-atmospheric pressure to said water outlet conduit, collecting the withdrawn water in a collection container separate from said separating chamber, continuously withdrawing the gas from the upper end of the chamber through a gas outlet conduit by applying a sub-atmospheric pressure to said gas outlet conduit, regulating the flow through the respective conduits whereby the flow through said water discharge conduit is substantially less than the flow through said gas outlet conduit, and analyzing the gas withdrawn through said outlet conduit.

2. A method of respiratory gas analysis, comprising the steps of conducting a respiratory gas sample from a patient to a water separating chamber having a tapered lower end, separating the water from the gas in said chamber, continuously withdrawing the separated water from the lower tapered end of the chamber through a first outlet conduit by applying sub-atmospheric pressure to said first conduit, connecting an emptiable water collecting container in said first conduit, collecting withdrawn water in said container, continuously withdrawing gas from the upper end of said chamber through a second conduit by applying a sub-atmospheric pressure to said second conduit, and analyzing the gas withdrawn through said second conduit.

* * * * *